US00PP22272P2

(12) United States Plant Patent
Ingemann Pedersen

(10) Patent No.: US PP22,272 P2
(45) Date of Patent: Nov. 22, 2011

(54) ***LAVANDULA* PLANT NAMED 'PINK SUMMER'**

(50) Latin Name: *Lavandula stoechas*
Varietal Denomination: Pink Summer

(75) Inventor: Jens Ingemann Pedersen, Odense N (DK)

(73) Assignee: Gartneriet Tvilingegaarden A/S, Odense (DK)

( * ) Notice: Subject to any disclaimer, the term of this patent is extended or adjusted under 35 U.S.C. 154(b) by 0 days.

(21) Appl. No.: 12/927,730

(22) Filed: Nov. 22, 2010

(51) Int. Cl.
*A01H 5/00* (2006.01)

(52) U.S. Cl. ..... Plt./445

(58) Field of Classification Search ..... Plt./445
See application file for complete search history.

*Primary Examiner* — Kent L Bell
(74) *Attorney, Agent, or Firm* — C. A. Whealy

(57) ABSTRACT

A new and distinct cultivar of *Lavandula* plant named 'Pink Summer', characterized by its compact, upright and somewhat outwardly spreading plant habit; freely branching growth habit; dense and bushy plant form; early and freely flowering habit; purple-colored flowers with light violet-colored terminal flower bracts; flowers arranged in compact verticillasters on crowded spikes; and good garden performance.

2 Drawing Sheets

Botanical designation: *Lavandula stoechas.*
Cultivar denomination: 'PINK SUMMER'.

BACKGROUND OF THE INVENTION

The present invention relates to a new and distinct cultivar of *Lavandula* plant, botanically known as *Lavandula stoechas* and hereinafter referred to by the name 'Pink Summer'.

The new *Lavandula* plant is a product of a planned breeding program conducted by the Inventor in Odense, Denmark. The objective of the breeding program was to develop new compact *Lavandula* plants with attractive plant form and flower coloration.

The new *Lavandula* plant originated from a cross-pollination made by the Inventor in 2004 of two unnamed proprietary selections of *Lavandula stoechas,* not patented. The new *Lavandula* plant was discovered and selected by the Inventor in 2005 as a single flowering plant within the progeny of the stated cross-pollination in a controlled outdoor nursery environment in Odense, Denmark.

Asexual reproduction of the new *Lavandula* by terminal cuttings in a controlled greenhouse environment in Odense, Denmark since 2006 has shown that the unique features of this new *Lavandula* plant are stable and reproduced true to type in successive generations.

SUMMARY OF THE INVENTION

Plants of the new *Lavandula* have not been observed under all possible environmental conditions. The phenotype may vary somewhat with variations in environment such as temperature and light intensity, without, however, any variance in genotype.

The following traits have been repeatedly observed and are determined to be the unique characteristics of 'Pink Summer'. These characteristics in combination distinguish 'Pink Summer' as a new and distinct cultivar of *Lavandula* plant:

1. Compact, upright and somewhat outwardly spreading plant habit.

2. Freely branching growth habit; dense and bushy plant form.
3. Early and freely flowering habit.
4. Purple-colored flowers with light violet-colored terminal flower bracts; flowers arranged in compact verticillasters on crowded spikes.
5. Good garden performance.

Plants of the new *Lavandula* differ from plants of the parent selections primarily in plant habit and flower color.

Plants of the new *Lavandula* can be compared to plants of *Lavandula stoechas* 'Barcelona Bridal Pink', disclosed in U.S. Plant Pat. No. 15,697. Plants of the new *Lavandula* differ from plants of 'Barcelona Bridal Pink' in the following characteristics:

1. Plants of the new *Lavandula* and 'Barcelona Bridal Pink' differed in leaf, flower and terminal flower bract color.
2. Plants of the new *Lavandula* have longer terminal flower bracts than plants of 'Barcelona Bridal Pink'.
3. Plants of the new *Lavandula* flower for a longer period of time than plants of 'Barcelona Bridal Pink'.

Plants of the new *Lavandula* can also be compared to plants of *Lavandula stoechas* 'Barcelona Rose', disclosed in U.S. Plant Pat. No. 15,481. Plants of the new *Lavandula* differ from plants of 'Barcelona Bridal Pink' in the following characteristics:

1. Plants of the new *Lavandula* and 'Barcelona Rose' differed in leaf, flower and terminal flower bract color.
2. Plants of the new *Lavandula* have smaller inflorescences than plants of 'Barcelona Rose'.
3. Plants of the new *Lavandula* have longer peduncles than plants of 'Barcelona Rose'.
4. Plants of the new *Lavandula* flower for a longer period of time than plants of 'Barcelona Rose'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph at the top of the first sheet comprises a side perspective view of a typical flowering plant of 'Pink Summer' grown in a container.

The photograph at the bottom of the first sheet is a close-up view of a typical flowering stem of 'Pink Summer'.

The photograph at the top of the second sheet is a close-up view of a typical inflorescence of 'Pink Summer'.

The photograph at the bottom of the second sheet is a close-up view of the upper surface of a typical leaf of 'Pink Summer'.

DETAILED BOTANICAL DESCRIPTION

The aforementioned photographs, following observations and measurements describe plants grown during the summer in 11-cm containers in an outdoor nursery in Odense, Denmark and under conditions and practices which approximate those generally used in commercial *Lavandula* production. Plants were 38 weeks old when the photographs and description were taken. During the production of the plants, day temperatures ranged from 15° C. to 27° C. and night temperatures ranged from 3° C. to 15° C. In the following description, color references are made to The Royal Horticultural Society Colour Chart, 2007 Edition, except where general terms of ordinary dictionary significance are used.

Botanical classification: *Lavandula stoechas* 'Pink Summer'.

Parentage:

*Female, or seed, parent.*—Unnamed proprietary selection of *Lavandula stoechas,* not patented.

*Male, or pollen, parent.*—Unnamed proprietary selection of *Lavandula stoechas,* not patented.

Propagation:

*Type.*—Terminal vegetative cuttings.

*Time to initiate roots, winter.*—About 16 to 18 days at 20° C.

*Root description.*—Fine, fibrous.

Plant description:

*Form.*—Herbaceous perennial; compact, upright and outwardly spreading plant habit; broad inverted triangle.

*Growth habit.*—Vigorous.

*Crop time.*—After rooting, about 22 weeks are required to produce finished flowering plants in 11-cm containers.

*Branching habit.*—Freely branching habit, dense and bushy plant form.

*Plant height.*—About 20 cm.

*Plant width* (*spread*).—About 25 cm.

*Lateral branch description.*—Length: About 13 cm. Diameter: About 2 mm. Internode length: About 2 cm. Strength: Moderately strong. Aspect: Upright to somewhat outwardly spreading. Texture: Tomentose. Color, immature: Close to 144B. Color, mature: Close to 200C.

*Foliage description.*—Arrangement: Opposite, simple; sessile. Length: About 3 cm. Width: About 4 mm. Shape: Lanceolate. Apex: Acute. Base: Cuneate. Margin: Entire, revolute. Texture, upper and lower surfaces: Pubescent. Fragrance: Aromatic, pungent. Venation pattern: Pinnate. Color: Developing leaves, upper and lower surfaces: Close to 138A. Fully expanded leaves, upper surface: Close to 137C; venation, close to 137C. Fully expanded leaves, lower surface: Close to 138A; venation, close to 138A.

Flower description:

*Flower arrangement and shape.*—Single sessile flowers arranged in compact verticillasters on crowded spikes; freely flowering habit, about eight rows of flowers per verticillaster; flowers salverform with a two-lobed upper lip and a three-lobed lower lip.

*Natural flowering season.*—Long flowering period; flowering continuous from the spring through the summer in Denmark.

*Flower longevity on the plant.*—Longevity of individual flowers is highly dependent on weather conditions; flowers not persistent; terminal flower bracts persistent.

*Fragrance.*—None detected.

*Flower buds.*—Length: About 6 mm. Diameter: About 2 mm. Shape: Oblong. Color: Close to N79B.

*Inflorescence size.*—Height: About 2 cm to 2.5 cm. Diameter: About 1 cm.

*Flowers.*—Diameter: About 5 mm. Depth (height): About 8 mm.

*Petals.*—Lip length: About 2 mm. Lip width: About 1 mm. Lip shape: Roughly spatulate to oval. Lip: Rounded. Lip margin: Entire. Lip texture, upper and lower surfaces: Smooth, glabrous. Lip color: When opening and fully opened, upper surface: Close to N79B. When opening and fully opened, lower surface: Close to N79C.

*Terminal flower bracts.*—Quantity/arrangement: About four in a single whorl at inflorescence apex, occasionally up to eight in number. Length: About 2 cm. Width: About 7 mm. Shape: Oblong to obovate. Apex: Obtuse. Base: Cuneate. Margin: Entire, undulate. Texture, upper and lower surfaces: Pubescent. Color: Immature, upper and lower surfaces: Close to 84A; venation, close to 84A. Mature, upper and lower surfaces: Close to 84B; venation, close to 84B.

*Flower bracts.*—Arrangement: Each whorl of flowers subtended by a flower bract. Length: About 8 mm. Width: About 7 mm. Shape: Broadly ovate. Apex: Broadly acute. Base: Cuneate. Margin: Entire. Texture, upper surface: Tomentose. Texture, lower surface: Smooth, glabrous. Color, immature and mature, upper surface: Close to 146D tinted with close to 187B; towards the base, close to 146D; venation, close to 146A. Color, immature and mature, lower surface: Close to 146D; venation, close to 146A.

*Sepals.*—Arrangement: Five sepals fused into a campanulate tube. Length: About 5 mm. Width: About 2 mm. Shape: Lanceolate. Apex: Four have acute apexes; the apex of the fifth sepal is rounded. Margin: Entire. Texture, upper surface: Tomentose. Texture, lower surface: Pilose. Color, immature and mature, upper surface: Close to 146D tinted with close to 187B; towards the base, close to 147D. Color, immature and mature, lower surface: Close to 146C; towards the base, close to 147D.

*Peduncles.*—Length: About 6 cm to 7 cm. Diameter: About 1 mm. Strength: Strong. Aspect: Mostly upright. Color: Close to 143C.

*Reproductive organs.*—Stamens: Quantity per flower: Four. Filament length: About 1 mm. Anther shape:

Reniform. Anther length: About 0.5 mm. Pollen amount: Moderate. Pollen color: Yellow. Pistils: Quantity per flower: One. Pistil length: About 5 mm. Stigma shape: Club-shaped. Stigma color: Dark red purple. Style length: About 4 mm. Style color: Whitish. Ovary color: Yellow green.

*Seeds.*—Length: About 2 mm. Diameter: About 2 mm.

Disease/pest resistance: Plants of the new *Lavandula* have not been noted to be resistant to pathogens and pests common to *Lavandula*.

Garden performance: Plants of the new *Lavandula* have exhibited good tolerance to rain and wind and hardy to USDA Hardiness Zone 7.

It is claimed:

1. A new and distinct *Lavandula* plant named 'Pink Summer' as illustrated and described.

* * * * *

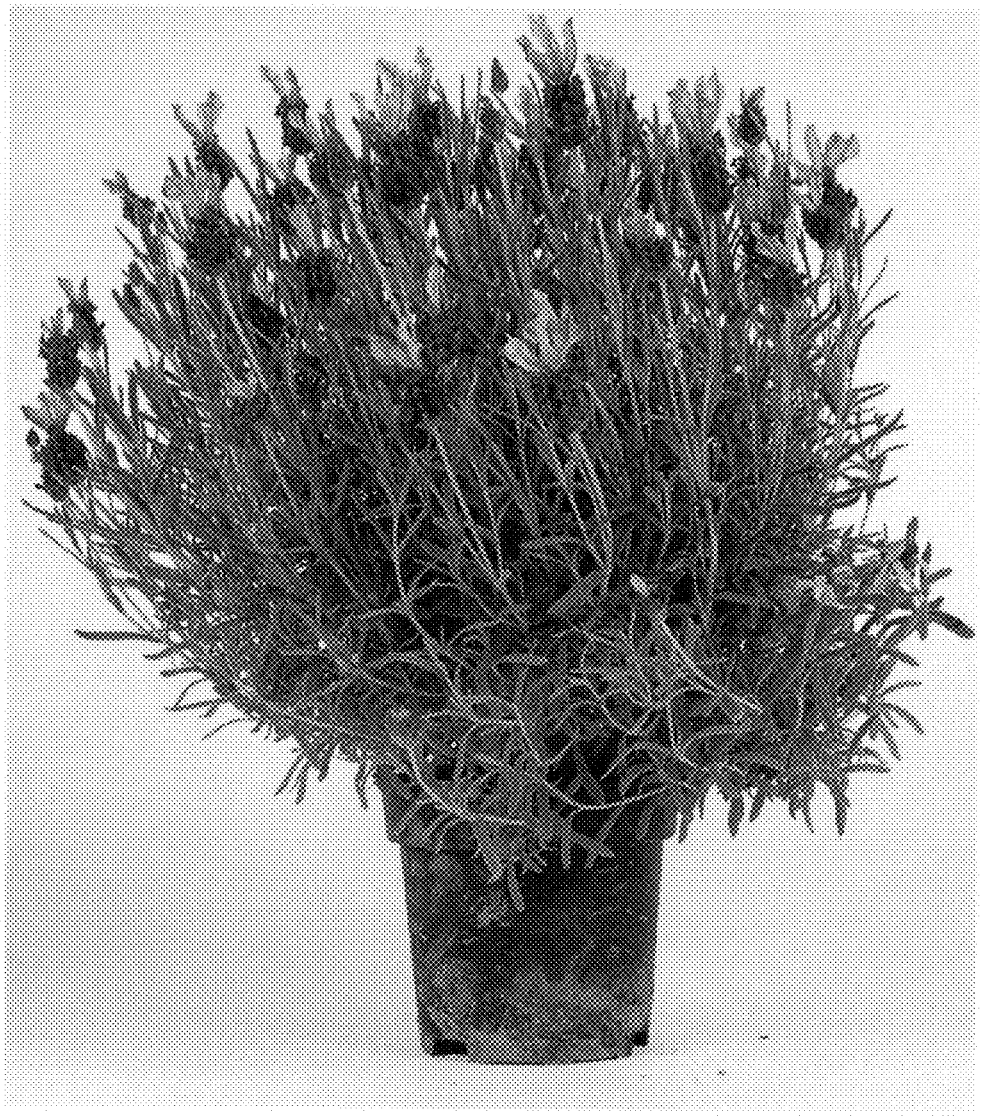
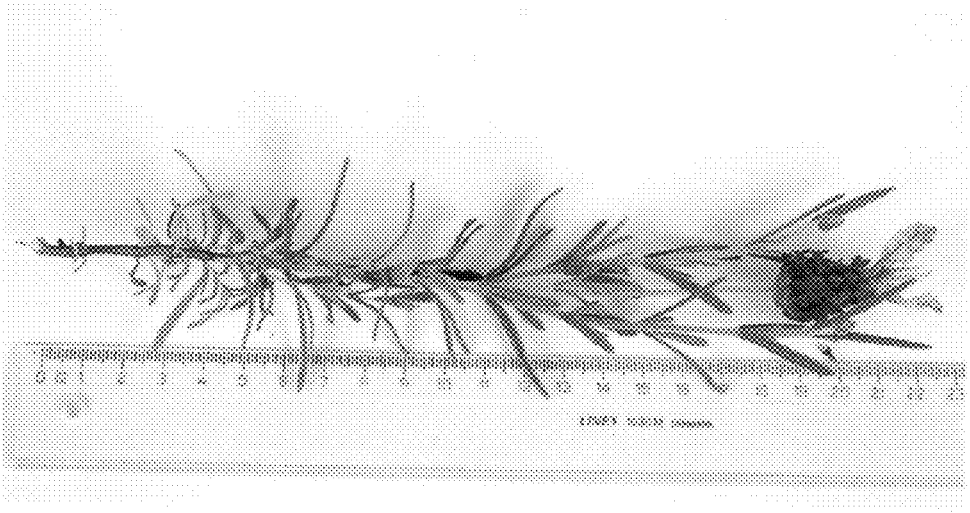

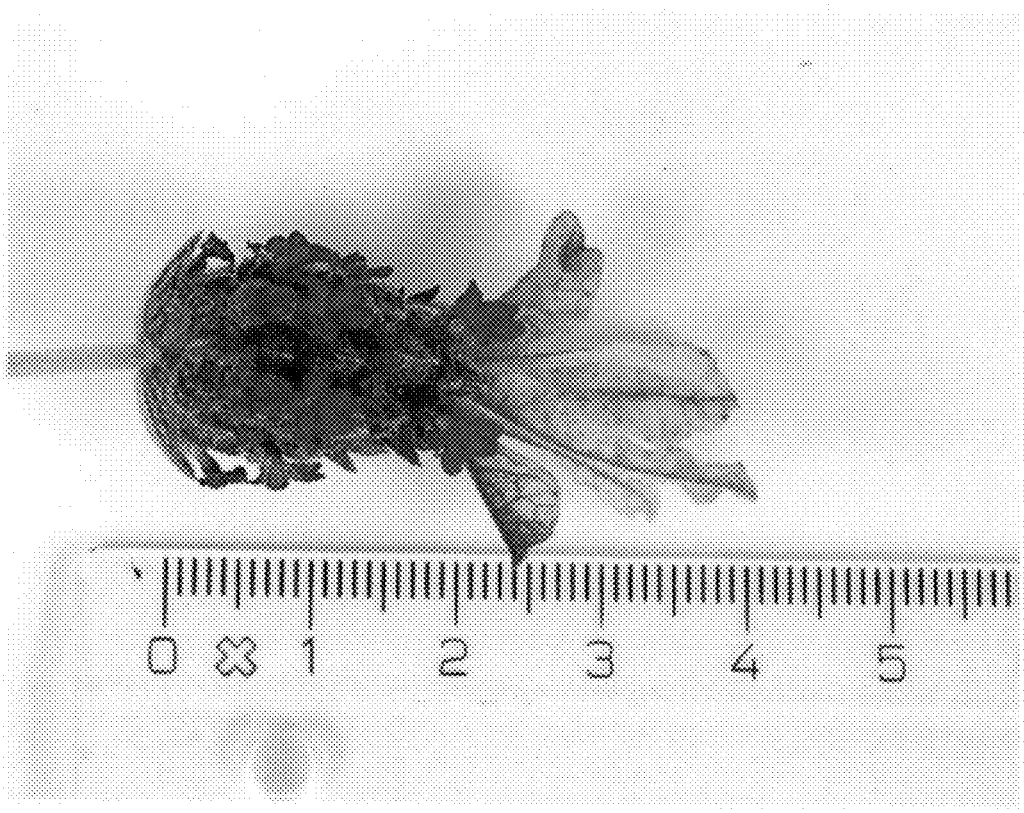
0 1 2 3 4 5
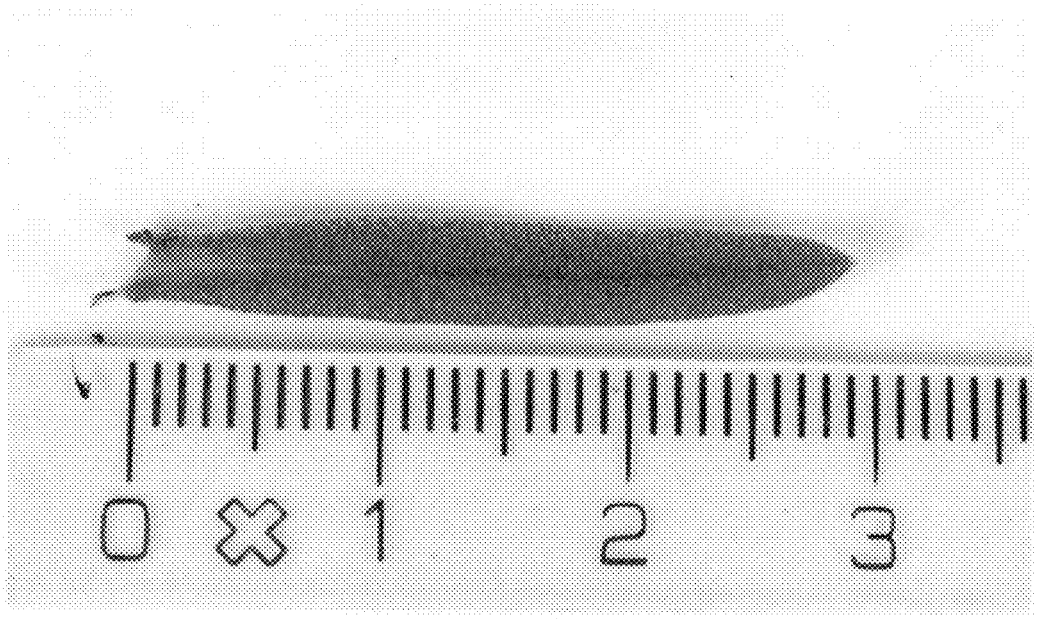
0 1 2 3